US009931153B2

(12) United States Patent
Thralls (10) Patent No.: US 9,931,153 B2
(45) Date of Patent: Apr. 3, 2018

(54) THERMOCHEMICAL REACTION ABLATION CATHETER

(71) Applicant: Spiration, Inc., Redmond, WA (US)

(72) Inventor: Christopher Thralls, Kirkland, WA (US)

(73) Assignee: Spiration, Inc., Redmond, WA (US)

(*) Notice: Subject to any disclaimer, the term of this patent is extended or adjusted under 35 U.S.C. 154(b) by 849 days.

(21) Appl. No.: 14/199,155

(22) Filed: Mar. 6, 2014

(65) Prior Publication Data

US 2014/0276577 A1 Sep. 18, 2014

Related U.S. Application Data

(60) Provisional application No. 61/790,133, filed on Mar. 15, 2013.

(51) Int. Cl.
| | |
|---|---|
| A61B 18/06 | (2006.01) |
| A61B 18/02 | (2006.01) |
| A61B 18/04 | (2006.01) |
| A61B 18/00 | (2006.01) |

(52) U.S. Cl.
CPC ........... *A61B 18/06* (2013.01); *A61B 18/02* (2013.01); *A61B 18/0218* (2013.01); *A61B 18/04* (2013.01); *A61B 2018/00642* (2013.01); *A61B 2018/00678* (2013.01); *A61B 2018/00702* (2013.01); *A61B 2018/00791* (2013.01); *A61B 2018/00863* (2013.01); *A61B 2018/0212* (2013.01); *A61B 2018/0262* (2013.01); *A61B 2018/046* (2013.01); *A61B 2218/007* (2013.01)

(58) Field of Classification Search
CPC ..... A61B 18/02; A61B 18/0218; A61B 18/04; A61B 18/06; A61B 2018/00642; A61B 2018/00678; A61B 2018/00702; A61B 2018/00791; A61B 2018/00863; A61B 2018/0212; A61B 2018/0262; A61B 2018/046; A61B 2218/007
See application file for complete search history.

(56) References Cited

U.S. PATENT DOCUMENTS

| | | | |
|---|---|---|---|
| 7,914,564 B2 | 3/2011 | Magers et al. | |
| 8,343,202 B2 | 1/2013 | Magers et al. | |
| 8,454,598 B2 | 6/2013 | Whayne et al. | |
| 2002/0151880 A1* | 10/2002 | Lafontaine | A61B 18/02 606/21 |
| 2010/0145304 A1 | 6/2010 | Cressman | |
| 2012/0046656 A1 | 2/2012 | Brannan | |
| 2012/0215212 A1 | 8/2012 | Selzer et al. | |
| 2012/0323213 A1 | 12/2012 | Bates | |

OTHER PUBLICATIONS

International Search Report and Written Opinion of related Application PCT/US2014/021478.

* cited by examiner

*Primary Examiner* — Imani Hayman (57) ABSTRACT

Embodiments disclosed herein are directed to devices, methods, and systems for the treatment of tissue using energy delivery. Specifically, certain embodiments may utilize a thermochemical reaction between at least two reagents where a first reagent has been preloaded into a catheter while a limiting reagent is circulated through the catheter to react with the first reagent. The resulting chemical reaction may be exothermic or endothermic, and a heat transfer fluid may be used to exchange energy between the chemical reaction and surrounding tissue.

11 Claims, 3 Drawing Sheets

THERMOCHEMICAL REACTION ABLATION CATHETER

CROSS REFERENCE TO RELATED APPLICATIONS

This application claims priority to and the benefit of U.S. provisional patent application Ser. No. 61/790,133 filed on Mar. 15, 2013 entitled "Thermochemical Reaction Ablation Catheter," the entire disclosure of which is hereby incorporated by reference as if set forth in its entirety for all purposes.

BACKGROUND

Technical Field

The present disclosure generally relates to the treatment of tissue via energy delivery. More particularly, certain embodiments of the present disclosure relate to thermal ablation of lung tissue with energy delivered via a piercing needle.

Description of the Related Art

Lung cancer, especially when presented in the form of cancerous nodules, has a high incidence of morbidity and mortality in patients. Early stages of lung cancer can take the form of solitary pulmonary nodules (in particular those under 5 mm in size) and may require careful evaluation by a medical professional, especially in patients that have risk factors such as tobacco use or a family history of cancer.

Lung nodules, other cancerous or pre-cancerous regions of tissue in the lung, and other tissue lesions may be difficult to treat with invasive surgical techniques, with attendant complications such as excessive bleeding, infection risk, air leaks, pneumothorax, and other such issues. In particular, regions deep in the lung may be difficult to access using conventional methods, further increasing the difficulty of treatment.

A number of ablation treatments have been used to treat tumors or other tissue in a patient's body. In some cases, ablation therapy may be used to treat tumors that are not responsive to chemotherapy or other techniques. Ablation treatments come in the form of RF ablation, microwave ablation to destroy the tumor tissue with heat, cryoablation to freeze a tumor. Thermochemical ablation can also be used and can be used to destroy tumors by either heat or freezing depending on the reactants used.

Much of the technology used for the treatment of suspect or cancerous tumors in the body requires general surgery or the use of expensive capital equipment with a large suite of specially tools.

SUMMARY

The present disclosure provides a variety of methods and devices some of which are meant to be standalone devices and, in some cases, to provide a minimally invasive (e.g., endoscopic) therapy option. According to some embodiments of the present disclosure, a device for the delivery or removal of energy to a region of a patient is disclosed where the device includes a catheter shaft configured to be inserted into the patient to reach a treatment region, a first reagent positioned in the catheter shaft at about a distal region of the catheter shaft, a first lumen positioned within the catheter shaft configured to deliver a limiting reagent to the distal region of the catheter shaft where the limiting reagent and the first reagent at least partially react with each other in a thermochemical reaction to produce a reaction product, a second lumen positioned within the catheter shaft configured to extract the reaction product from the distal region of the catheter shaft, a third lumen positioned within the catheter shaft configured to transport a heat transfer fluid. In some embodiments, the heat transfer fluid is configured to transfer energy between the treatment region and the reaction product. Some embodiments include a handle attached at a proximal end of the catheter shaft, and the handle is configured to control at least one of a flow of the limiting reagent into the catheter shaft, a flow of the heat transfer fluid into the catheter shaft, and a flow rate of the reaction product.

According to some embodiments, the heat transfer fluid is configured to flow out of the catheter shaft at about the distal region. And in some embodiments, the handle is further configured to control the flow of the heat transfer fluid out of the catheter shaft.

The thermochemical reaction in some embodiments is selected from the following list: crystallization of supersaturated liquid salts, oxidation of metals, acid reactions, thermite reactions, acid/base reactions, oxidation reactions, and hydration reactions, etc. In some embodiments, the thermochemical reaction is exothermic, and the reaction product transfers energy to the heat transfer fluid. In some embodiments, the thermochemical reaction is endothermic, and the heat transfer fluid transfers energy to the reaction product. At least one of the reagents can be a solid that has been placed in the catheter shaft prior to the catheter shaft being inserted into the patient's body.

According to some embodiments, the catheter is dimensioned to be insertable into a bronchoscope. And in some embodiments, the bronchoscope comprises a side-facing ultrasound probe. The handle can further comprise a bronchoscope attachment configured to attach to the working channel of a bronchoscope. And the bronchoscope attachment comprises a bronchoscope guide configured to be inserted at least partially into the working channel of the bronchoscope. In some embodiments, a catheter shaft includes a guide sheath disposed over at least a portion of the catheter shaft.

According to some embodiments, the heat transfer fluid comprises a medicant. In some embodiments, a catheter shaft includes an extraction lumen 160 configured to extract at least some of the heat transfer fluid that has been allowed to flow out of the distal region of the catheter shaft. In some cases, the handle is configured to control the flow of the heat transfer fluid that is extracted from the patient's body. And in some cases, a fourth lumen 176 is included that is configured to extract the heat transfer fluid from the catheter shaft such that the heat transfer fluid circulates within the catheter shaft without flowing out of the catheter shaft into a patient's body.

According to some embodiments, a catheter shaft includes a plurality of sensors configured to monitor inlet and outlet temperatures of the heat transfer fluid. In some embodiments, a sensor is included that is configured to detect the temperature of the reaction product at about the distal region of the catheter shaft. And in some cases, a sensor is configured to detect the temperature of the surrounding tissue.

According to some embodiments, a feedback mechanism is used to adjust the amount of energy transfer occurring between the reaction product and tissue of the treatment region in response to one or more monitored attributes. In some embodiments, the monitored attributes are selected from the group consisting of tissue temperature, reaction product temperature, flow of heat transfer fluid out of the distal region of the catheter shaft, and time. In some embodiments, a feedback mechanism is configured to stop the flow of limiting reagent and/or heat transfer fluid in response to a level of monitored attributes exceeding a predetermined limit.

According to some embodiments of the present disclosure, a method of delivering energy to a region of a patient's body to be treated is disclosed where the method includes inserting a catheter into an interior portion of a patient's body, navigating the catheter to a treatment region within the patient's body, activating the flow of a limiting reagent to the catheter, and transferring energy between the catheter and the treatment region. In some embodiments, the catheter includes a first reagent positioned in the catheter shaft at or about a distal region of the catheter shaft, a first lumen configured to deliver a limiting reagent to the distal region of the catheter where the limiting reagent and the first reagent react with each other in a thermochemical reaction to produce a reaction product, a second lumen positioned within the catheter configured to extract the reaction product from the catheter, and a third lumen 156 positioned within the catheter shaft configured to transport a heat transfer fluid.

In some embodiments, the thermochemical reaction is exothermic, and in some embodiments, the reaction is endothermic. In some embodiments, the thermochemical reaction is selected from at least one of the following: crystallization of supersaturated liquid salts, oxidation of metals, acid reactions, thermite reactions, acid/base reactions, oxidation reactions, and hydration reactions.

In some embodiments, a heat transfer fluid is ejected from a distal region of the catheter toward the treatment region. In some embodiments, at least some of the heat transfer fluid that has been ejected toward the treatment region is extracted from the treatment region using a fourth lumen in the catheter. Some embodiments include monitoring at least one monitored attribute associated with the transfer of energy between the treatment and the heat transfer fluid. The monitored attribute can be selected from the group consisting of treatment region temperature, reaction product temperature, and time. The amount of energy transferred can be adjusted in response to a feedback mechanism responsive to at least one monitored attribute. And in some embodiments, energy exchange between the treatment region and the catheter can be stopped in response to a level of the monitored attributes exceeding a predetermined limit.

According to some embodiments of the present disclosure, a system for the transfer of energy between a treatment region of a patient's body and a heat transfer fluid includes an energy transfer device, a limiting reagent fluid source, a heat transfer fluid source, and a conduit insertable into the patient's body. The energy transfer device can include a catheter configured to be inserted into the patient's body where the catheter includes at least a first, second, and third lumens. The energy transfer device can also include a handle attached at a proximal end of the catheter where the handle configured to control at least one of the flow of a limiting reagent through the first lumen, the flow of a reaction product out of the catheter through the second lumen where the reaction product is the result of a thermochemical reaction between the limiting reagent and a solid reagent, the flow of a heat transfer fluid through the third lumen. In some embodiments, the conduit is selected from the group consisting of a bronchoscope and guide sheath, the catheter being insertable and movable therein.

In some embodiments, a system for the transfer of energy can further include at least one sensor configured to monitor at least one monitored attribute of the system. And the monitored attributes can be selected from temperature at one or more locations of the catheter, fluid flow rate of one or more of the limiting reagent, the reaction product, and the heat transfer fluid. In some embodiments, a system for the transfer of energy can further include a feedback system responsive to at least one of the monitored attributes, wherein the feedback system is configured to change or stop one or more treatment attributes.

BRIEF DESCRIPTION OF THE DRAWINGS

These and other features, aspects and advantages of the present disclosure will now be described with reference to several drawings, which drawings are intended to be illustrative and not limiting.

DETAILED DESCRIPTION

Embodiments of an apparatus, system, and method for identification and treatment of cancerous tumors will be described with reference to the accompanying figures of one or more embodiments. The terminology used in the description presented herein is not intended to be interpreted in any limited or restrictive manner. Rather, the terminology is simply being utilized in conjunction with a detailed description of embodiments of the systems, methods and related components. Furthermore, embodiments may comprise several novel features, no single one of which is solely responsible for its desirable attributes or is believed to be essential to practicing the inventions herein described.

The terms "lung region," "lung area," "tumor," "tissue," "lesion" and "nodule" as used herein are broad interchangeable terms and, unless otherwise indicated or apparent from the context of use, the terms can include within their meaning, and without limitation, other organs or regions of tissue in a human or animal body, including diseased, cancerous, and/or pre-cancerous tissue, as well as tissue showing lesions, or generally any tissue region for which treatment is desired. Although some embodiments described herein refer to identifying and treating an area within a lung, this disclosure is not so limited, and the embodiments described herein may be used, for example, in other vessels, passages, body cavities, and organs in humans and animals.

According to some embodiments of the present disclosure, a catheter system is disclosed, the system comprising an insertion tube containing a number of lumens, the tube being connected to a handle. The catheter system is used to deliver heat to or extract heat from a treatment area such as a cancerous growth or tumor. The heat delivery or extraction can be accomplished using one or more thermochemical reactions that either produce or consume energy. In some embodiments, one or more reactants are brought into contact within the insertion tube and are not allowed to leak out into or contact a patient's tissue. In some embodiments, only energy transfer occurs with essentially no materials entering or exiting a patient's body during a procedure. In some embodiments, a heat transfer fluid is allowed to flow out of the insertion tube to interact with the treated tissue.

In some embodiments, an insertion tube comprises a number of lumens including one lumen in which is packed or located one or more first reactants that may be in solid form. A second reactant can flow through the same lumen thereby reacting with the first reactant to produce energy in the form of heat. In some embodiments, the resulting reaction actually consumes energy thereby cooling the insertion tube and any surrounding materials or tissue. The reaction products can then be extracted through the same or a different lumen so to not enter the patient's body.

In some embodiments, an insertion tube comprises at least three lumens. The first lumen can be used to transport a first reagent toward a distal region of the insertion tube to react with a second reagent. The second lumen can be used to transport the reaction products of the first and second reagents away from the distal region of the insertion tube toward a proximal region of the tube. The first and second lumens will generally be in fluid communication with each other. The third lumen can be used to transport a heat transfer fluid toward the distal region of the insertion tube. In some embodiments, the heat transfer fluid is allowed to exit the insertion tube at or near the distal region. Some embodiments include a fourth lumen that can be used to extract the heat transfer fluid from the distal region of the insertion tube. In some embodiments, the heat transfer fluid is extracted from the treated area of the patient's body. In some embodiments, the third and fourth lumen may not be in fluid communication with each other.

While the embodiments disclosed herein may be described as comprising one, two, three, or four lumens, it will be understood that other configurations could also be used to optimize or maximize the heat transfer between a reaction and a treatment area. Moreover, any variety of geometries could be used to maximize or optimize the transfer of heat from a chemical reaction to a heat transfer. For example, multiple heat transfer fluids could be used, which may require separate lumens for each fluid. And more than two reagents could be used and could similarly require additional lumens. In some embodiments, fewer reagents could be used or the heat transfer fluid and the reaction product may comprise the same material thereby, which could allow for the use of fewer lumens.

According to some embodiments, a handle (e.g., handle 200 of FIG. 1) is attached to a proximal region of the insertion tube. The handle can be configured to control and/or monitor any number of variables such as, but not limited to, a flow rate of a first reagent into the insertion tube, a flow rate of any reaction products out of the insertion tube, a flow rate of a heat transfer fluid into the insertion tube, a flow rate of a heat transfer fluid out of the insertion tube and into a patient, a flow rate of a heat transfer fluid being extracted from a patient's body, a temperature at one or more locations of the insertion tube, a duration of a procedure, an extent of ablation or other procedure, etc. The handle can include readouts (e.g., a display) of one or more of the parameters monitored by the handle. The temperature could be monitored using one or more thermocouples, though other sensor types could be used to monitor the temperature. In some embodiments, at least one of a first reagent, a heat transfer fluid, and reaction products flows through the handle. In some embodiments, the handle affects the flow of at least one of a first reagent, a heat transfer fluid, and reaction products even if those fluids do not actually flow through the handle. In some embodiments, only fluids flowing into the insertion tube flow through the handle while fluids flowing out of the insertion tube do not flow through the handle.

A handle according to the present disclosure is generally external to a patient's body and may be easily manipulated by a doctor, nurse, technician, etc. In some embodiments, the handle controls the flow of the limiting reagent. The rate heat transfer may be controlled by adjusting the flow of a limiting reagent and/or the flow of a heat transfer fluid. In some embodiments, the temperature of a heat transfer fluid is monitored at one or more points along the fluid's flow path. For example, the incoming temperature may be monitored, though other temperatures may also or alternatively be monitored. In some embodiments, the inlet and outlet temperatures of a heat transfer fluid are monitored. In some embodiments, a heat transfer fluid may be recirculated to achieve a desired temperature profile or rate of heat transfer.

According to some embodiments of the present disclosure, a heat transfer fluid is used to transfer heat to or from a chemical reaction that occurs in an insertion tube. In some embodiments, the heat transfer fluid is biocompatible. Biocompatibility may be desirable when there is a risk that the fluid may leak from the insertion tube and enter a patient's body. Biocompatibility may be necessary in some embodiments in which the heat transfer fluid is actually injected into a patient's body and may be aspirated back out.

In some embodiments, the heat transfer fluid may comprise an aqueous liquid such as water or a water-based fluid, such as a saline solution. Other fluids could also be used such as oils, liquid polymers, etc. Fluids more viscous than water can be used. Viscous fluids may advantageously flow into a treatment area without draining away as quickly as water or another less viscous fluid. While the fluid may be a liquid, in some embodiments it may be a gel or other flowable substance.

In some embodiments of an insertion tube according to the present disclosure, a chemical reaction occurs within the insertion tube. The chemical reaction may be the result of the interaction between two or more reagents. In some embodiments, a first reagent flows into the insertion tube, and a second reagent is pre-loaded in the insertion tube. The first reagent may be referred to as the non-limiting reagent, and the second reagent may be referred to as the limiting reagent. The first reagent may be a liquid, gas, or solid; and the second reagent may be a liquid, gas, or solid. In some embodiments, at least one reagent is a solid within an emulsion capable of flowing through the insertion tube.

In some embodiments, the reaction between the multiple reagents is exothermic, which can be useful in a number of procedures, such as denaturing proteins. In some embodiments, the reaction between the multiple reagents is endothermic, which can be useful in a number of procedures, such as cryoablation. The chemical reaction may be the result of any number of known or predictable reactions, which include but are not limited to crystallization of supersaturated liquid salts, oxidation of metals, acid reactions, thermite reactions, acid/base reactions, oxidation reactions, hydration reactions, etc. In some embodiments, catalyzed hydrogen can be reacted with oxygen with the use of a palladium sponge. Of course, one of skill in the art will recognize that other reactions could easily be incorporated into the various embodiments disclosed herein. According to some embodiments, toxic reagents or chemical reactions that produce toxic products may be used and neither the reagents nor the reaction products may be allowed to exit the insertion tube to enter a patient's body. In some embodiments, the use of a heat transfer fluid may facilitate the transfer of heat from such reactions to a treatment area of the body even if the reagents or reaction products do not physically interact with the treatment area.

Possible reducing reagents include, but are not limited to, glycerol, dextrin, maltodextrin, glucose, sucrose, hydrogen peroxide, iron(II) ammonium sulfate, titanium trichloride, cuprous chloride, stannous sulfate, sodium thiosulfate, etc. Possible oxidizing reagents include, but are not limited to, permanganate, sodium hypochlorite, sodium peroxide, iron (II) ammonium sulfate, ammonium persulfate, etc.

Thermite fuels for use in a thermite reaction include, but are not limited to, aluminum, magnesium, calcium, titanium, zinc, silicon, boron, etc. Such fuels can be oxidized by boron(III) oxide, silicon(IV) oxide, chromium(III) oxide, copper(II) oxide, iron(III) oxide, iron(II,III) oxide, copper (II) oxide, lead (II,II,IV), etc.

Possible reagents for use in a hydration reaction include, but are not limited to, calcium oxide, sulfuric acid, potassium hydroxide, sodium hydroxide, etc.

In an acid base reaction, possible acids include, but are not limited to, acetic acid, oxalic acid, peracetic acid, hydrochloric acid, hydrobromic acid, hydriodic acid, sulfuric acid, nitric acid, nitrous acid, perchloric acid, phosphoric acid, oxalic acid, pyruvic acid, malonic acid, amino acids (e.g., carboxylic acid derivative), chloric acid, etc. Possible bases include, but are not limited to, alanine, ammonia, methylamine, pyridine, potassium hydroxide, barium hydroxide, caesium hydroxide, strontium hydroxide, lithium hydroxide, rubium hydroxide, magnesium hydroxide, sodium hydroxide, ammonium hydroxide, calcium hydroxide, sodium bicarbonate, potassium carbonate, butyl lithium, sodium ethoxide, sodium ethanethiolate, sodium hydride, potassium hydride, some amines, etc.

The reaction between one or more reagents can be facilitated, in some embodiments, by configuring the lumen, or lumens, in which the reaction occurs to achieve the greatest extent of the reaction. For example, a lumen may be designed to induce a particular fluid flow to encourage a thorough interaction and reaction between multiple reagents. Particular fluid flows may also facilitate the transfer of heat between reaction products and a heat transfer fluid. In some embodiments, a spiral element is included within the lumen containing the reaction, where the spiral element induces mixing between the reagents. Similarly, the fluid flow of a heat transfer fluid may be manipulated to increase the extent of energy transfer between it and reaction products and/or the exterior of an insertion tube.

According to some embodiments of the present disclosure, an insertion tube is configured to or is capable of use with a bronchoscope or an endoscope. In some embodiments, an insertion tube is sufficiently flexible for easy insertion and manipulation in a tube or a patient's body. In some embodiments, the insertion tube can be inserted into a patient's body without the assistance of either a bronchoscope or an endoscope. Treatment into mid-lung region can be performed using bronchoscope-based treatment methods. Some embodiments are compatible with ultra-thin endoscopes and guide sheath systems which may allow the insertion tube to reach difficult to reach locations without causing excessive tissue aggravation. In particular, bronchoscopes with side-facing ultrasound probes (such as the Olympus EBUS® scope) may be particularly well suited for treatment of regions of lung tissue such as lung nodules (e.g., tumors, lesions, masses, nodules, or other areas of interest in the lung inside of or outside of the lung airways):

Peripheral regions of the lung may comprise subsegmental bronchi leading to terminal bronchi and alveoli, and may be too small or too highly angulated to be navigated with traditional visualization means. Navigating to and treating such peripheral regions may thus require a bronchoscope or other guide means to be inserted as far as possible, followed by extension of a much smaller guide sheath into the peripheral regions. Guidance to the peripheral region in such cases may be provided using fluoroscopy or other non-bronchoscopic visualization methods. These methods may also be useful in larger airways that are highly angulated and thus difficult or impossible to reach via bronchoscopic approaches.

Bronchoscopes or other endoscopes provided with ultrasound probes or otherwise used in conjunction with ultrasound may also be used in conjunction with Doppler or other blood flow visualization means. Especially in a highly-vascularized environment such as the lung, visualization of blood flow may be advantageous to avoid causing excessive bleeding or delivering large amounts of energy to blood vessels.

In some embodiments of a catheter system configured to be guided to positions within peripheral lung regions, the catheter system (which may still be disposed within a guide sheath) may be guided using external guidance methods. For example, guidance may be effectuated via real time computerized tomography ("CT"), via electromagnetic navigation (e.g., the SuperDimension iLogic system), via various transthoracic tools, or via fluoroscopy.

According to some embodiments of the present disclosure, a thermochemical insertion tube provides a low cost treatment option for cancerous tumors, nodules, lymph nodes, etc. The locations of the target area to be treated can be predetermined by doctor, nurse, technician, or other medical professional. In some embodiments, a medical professional will position the insertion tube or ablation/cryoablation catheter as close to the target tissue as possible. And by adjusting the flow rate of a heat transfer fluid and a quantity of limiting reagent 124, or second reagent, the reaction thermodynamics or heat generated and degree of heat transfer can be controlled and monitored, such as by way of the handle portion. In some embodiments, the catheter can be withdrawn when desired (e.g., when the desired amount of ablation/cryoablation has been performed).

Figure 1:
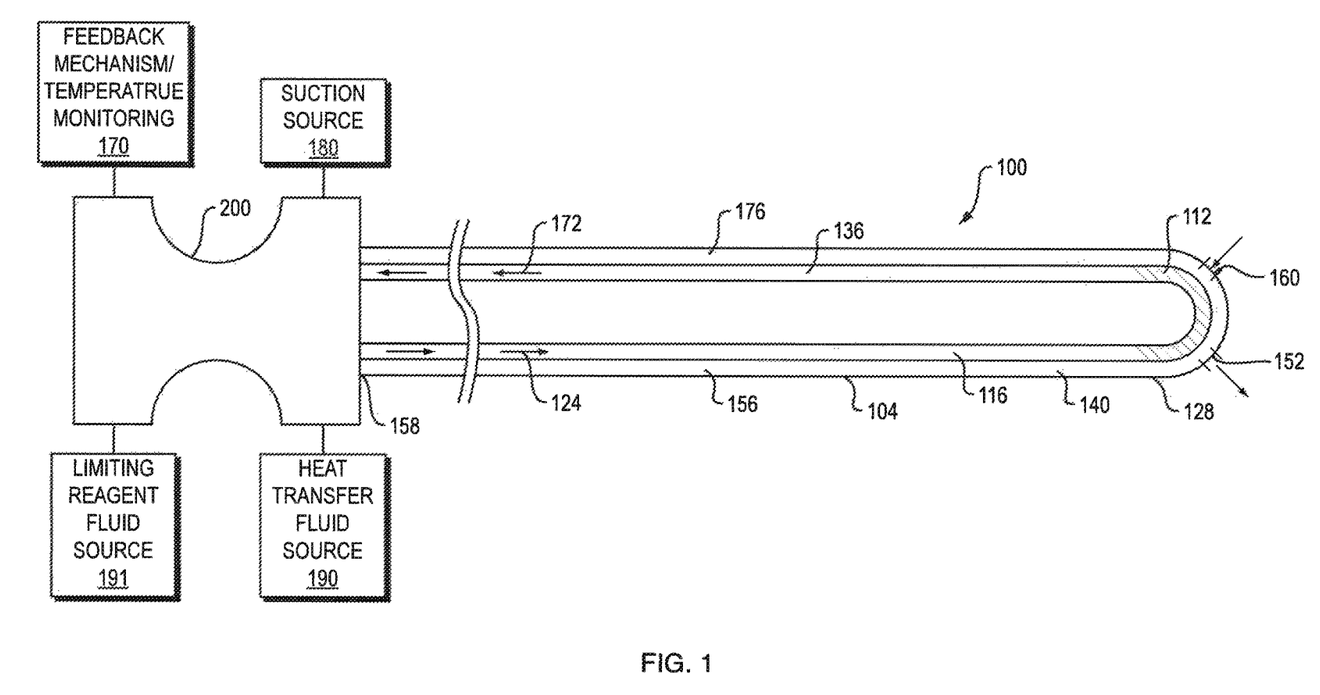
FIG. 1 is a schematic representation of an embodiment of a catheter system that is arranged and configured in accordance with certain features, aspects and advantages of an embodiment of the present disclosure.
Figure 2:
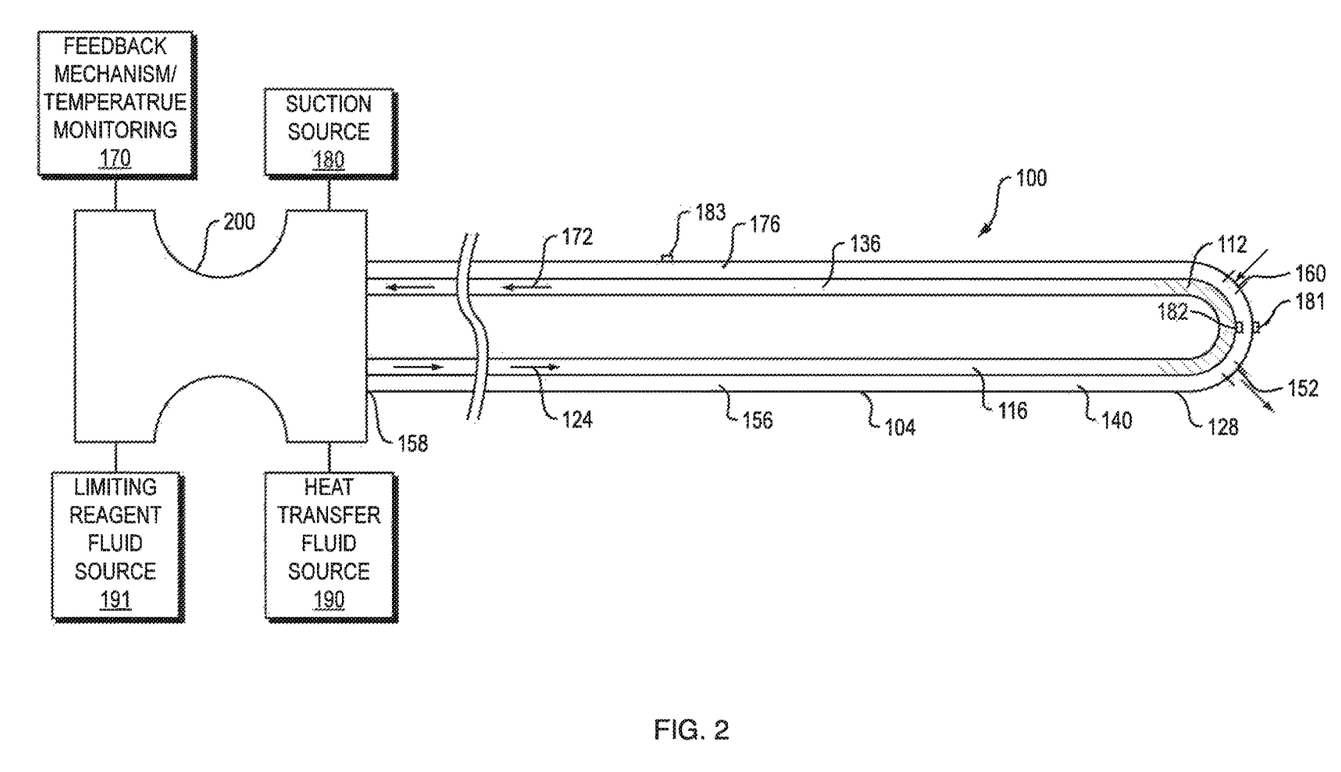
FIG. 2 is a schematic representation of an embodiment of a catheter system that is arranged and configured in accordance with an alternative embodiment of the present disclosure.
Figure 3:
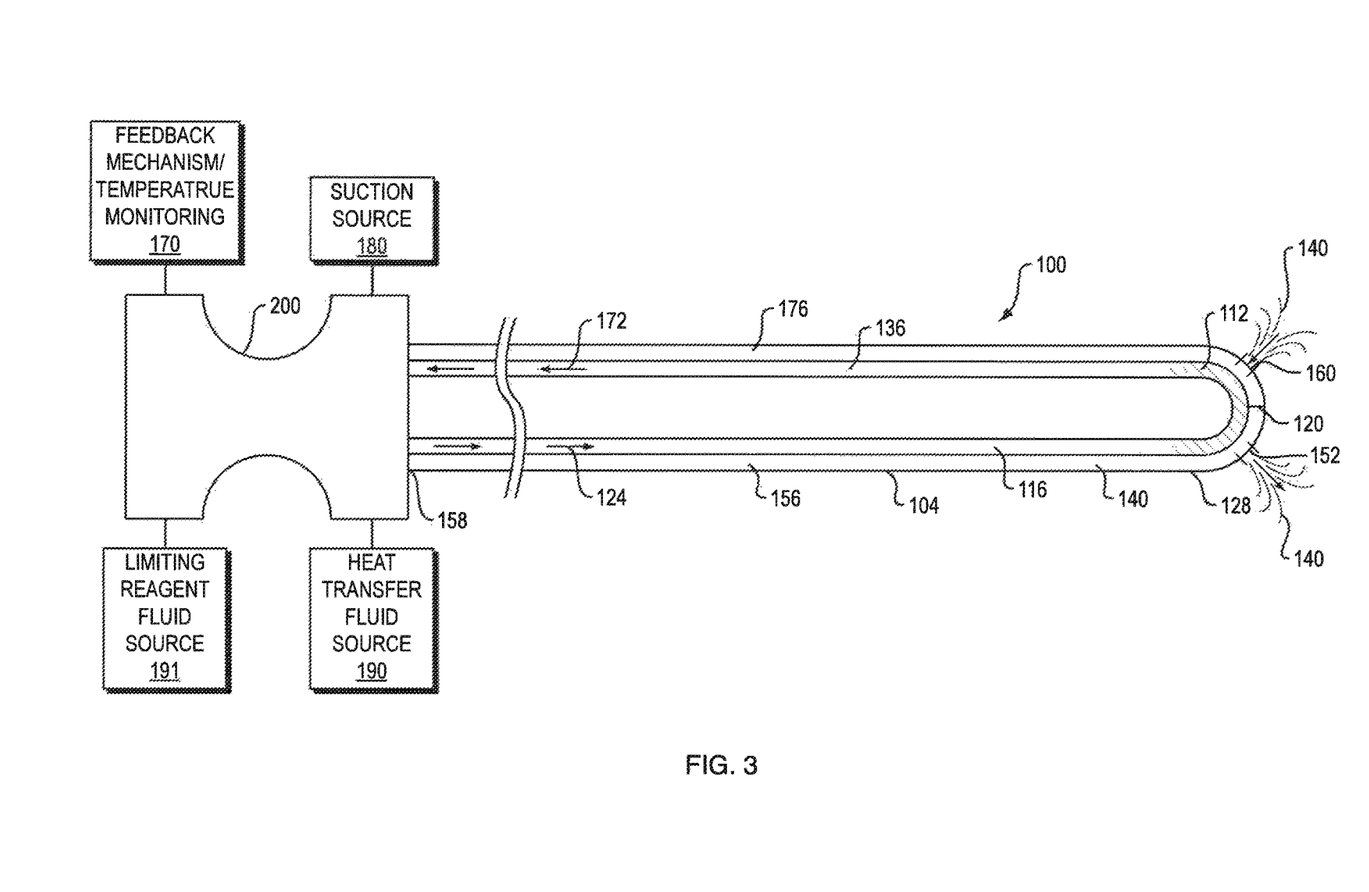
FIG. 3 is a schematic representation of an embodiment of a catheter system that is arranged and configured in accordance with an alternative embodiment of the present disclosure.

FIG. 1 illustrates a schematic representation embodiment of a catheter system 100 that is arranged and configured in accordance with certain features, aspects, and advantages of the present disclosure. The illustrated catheter system 100 comprises a catheter shaft 104 connected to a handle 200. The handle 200 preferably is configured to be gripped by one hand of a user (e.g., a doctor, nurse, or other health professional).

In some embodiments, the handle 200 is configured to control a variety of variables, such as the flow rate of a heat transfer fluid and/or the flow rate of one or more reagents. In some embodiments, the handle 200 controls an extraction rate of one or more reagents and/or an extraction rate of one or more heat transfer fluids. In some embodiments, the handle 200 controls a flow rate of one or more heat transfer fluids that exit the catheter shaft 104 and enter a patient's body near a treatment area.

According to some embodiments of the present disclosure, one or more reagents are used to produce or extract heat from a treatment area. To advantageously utilize such heat transfer, the one or more reagents can be transported through one or more lumens extending along the catheter shaft 104. A heat transfer fluid can be used to transfer the heat from the chemical reaction to the treatment area. In some embodiments, a heat transfer fluid extracts heat from the body transferring it instead to the cooled reaction products from an endothermic reaction. In some embodiments, a first reagent 112 flows into the catheter shaft 100 via a first lumen 116 while a second reagent 124 is located in a distal region 128 of the catheter shaft 104. The reaction product may remain in the catheter shaft 104, or it may be extracted as desired through the first lumen 116 or through a second lumen 136. Depending on the reaction kinetics and/or thermodynamics of the chemical reaction used, the second reagent 124 can be located upstream of the distal region 128 of the catheter shaft 104. Such a configuration may allow the first reagent 112 and second reagent 124 more time or distance to react or fully react thereby transferring more heat to or from a heat transfer fluid.

The heat transfer fluid 140 may enter the catheter shaft 104 at any suitable access point along the catheter shaft, the handle 200, or some other access point in the catheter system. FIG. 1 illustrates the heat transfer fluid 140 entering the catheter shaft 104 at entry point 158. In some embodiments, the heat transfer fluid 140 may be ejected or dispensed from the catheter shaft to interact with a treatment area. In some cases, an ejection port 152 can be located in the distal region 128 of the catheter shaft 104. During an ablation/cryoablation procedure, a medical profession can bring the ejection port into close proximity to a tumor or other tissue to be treated and ejects an appropriate amount of heat transfer fluid 140. In some embodiments, the heat transfer fluid 140 is either not ejected from the catheter shaft 104 or is at least partially extracted from a treated area. In some cases, the heat transfer fluid 140 may be extracted via an extraction port 160 and/or may exit from the catheter shaft 104 via an exit port 152. Heat transfer fluid 140 may be provided by heat transfer fluid source 190 and removed through the use of suction source 180.

In some embodiments, the heat transfer fluid 140 is circulated through the catheter shaft. Circulation can be used to increase the amount of energy transferred between the chemical reaction and the heat transfer fluid 140. According to some embodiments, circulation is used whether or not the heat transfer fluid 140 is ejected from the catheter shaft 104.

In some embodiments, a fluid source (e.g., a syringe, a pump) is connected to at least one of the lumens for example via tubes, hoses, lumens, and the like. In some embodiments, the fluid source connects to the handle 200. The fluid source can deliver to and/or extract fluid from the catheter system 100. The fluid source can be configured to deliver energy to a region of tissue via the catheter system 100, which includes one or more lumens. The fluid source may refer to a limiting reagent fluid source 191 or a heat transfer fluid source 190.

In some configurations, the fluid source comprises a source of a single reagent or multiple reagents. In some embodiments, the fluid source need only supply one reagent, for example if a second reagent is already located in a lumen of the catheter shaft 104. In some embodiments, the fluid source separately supplies multiple reagents to be mixed and reacted in the catheter shaft 104.

The amount of energy applied to or extracted from a treatment site can depend on, among other factors, the types of reagents, the flow rate of one or more reagents, the flow rate of the heat transfer fluid 140, and the duration of the procedure. Accordingly, in some configurations, the reaction rate can be set by a medical professional, and the resulting reactant flow will vary in accordance with that setting.

In particular, tissue such as tumors (especially lung nodules) or other tissue masses may be treated with energy so as to heat the cells therein to ablate, kill, burn, heat, or denature the cells. The tissue may not necessarily need to be heated so as to kill the component cells, but may be heated enough to modify the cells so as to become non-malignant or otherwise benign. As described above, in some configurations, this may also be achieved by cooling the respective tissue area, for example via cryoablation.

In some embodiments, the catheter shaft 104 is configured to deliver and/or facilitate heat at one or more points on the shaft's surface. Different embodiments can include the use of one or more exit ports, such as exit port 152. The various exit ports may be located at different points on the surface of the catheter shaft 104 rather than the single exit port 152 illustrated in the distal region 128 of the catheter shaft 104. Some embodiments can also or alternatively rely on heat transfer between the exterior surface of the catheter shaft 104 and the surrounding tissue without the use of heat transfer fluid 140 entering the treatment region. Moreover, the catheter shaft 104 can include one or more areas of heat transfer. The number and location of such areas can be determined by the reaction kinetics of the particular reaction used, for what extent the reaction is allowed to occur, and how the heat transfer fluid 140 is used to circulate or flow around the first lumen 116 and the second lumen 136. Heat transfer fluid 140 may flow through the third lumen 156 and be extracted through the fourth lumen 176. An additional lumen wall 120 may be provided in some embodiments such that the third lumen 156 and the fourth lumen 176 are not in direct fluid communication. In such a case, heat transfer fluid would flow out of port 152 from the third lumen 156, enter the surrounding tissue, and enter back into the catheter shaft 104 through port 160 and travel back toward the handpiece 200 through the fourth lumen 176. It is contemplated that in alternative embodiments, the position of the outer lumens 156 and 176 may be swapped with the inner lumens 116 and 136 such that the thermochemical reaction occurs in the outermost portion of the catheter shaft 104.

The catheter system 100 may be used for treatment of tissue, for example pulmonary tissue. In some configurations, the catheter shaft 104 can be inserted into a patient's airway so that the distal region 128 of the catheter shaft 104 reaches or is placed proximate a region of tissue to be treated. In some configurations, the catheter shaft 104 can be insertable into a bronchoscope. Various types of bronchoscopes may be used, including but not limited to the BF-P180 bronchoscope manufactured by Olympus. Bronchoscopes using ultrasound probes or other visualization devices also can be used, including the EBUS® scope manufactured by Olympus. The handle 200 of the catheter system 100 can generally be placed close to, or in contact with, the working channel of the bronchoscope. The handle may be placed at the proximal end 158 of the catheter shaft.

According to some configurations (e.g., when used relative to other body tissues and/or in other body lumens), the catheter system 100 can be loaded into other types of endoscopes.

Because the lungs generally have airway sizes of decreasing diameter and increased convolution, treatment modalities may need to be varied in response to the pulmonary area being treated. The central lung, extending from the trachea to the larger (i.e., left and right) main bronchi, and the mid-lung region, which may comprise lobar and segmental bronchi, can be large enough to be navigated with a bronchoscope. Accordingly, treatment of affected areas in the lung, which may include lung nodules and other such diseased regions, may be performed with relative ease in the central lung.

According to some embodiments of the present disclosure, the heat transfer fluid 140 may be used for several purposes. In some embodiment, the heat transfer fluid 140 acts to cool the first reagent 112, the second reagent 124, the reaction product 172, an internal or external surface of the catheter shaft 104, etc. Cooling the electrodes may be beneficial to maintaining performance during energy application to tissue.

The heat transfer fluid 140 may also be beneficial in preventing tissue charring when delivering energy that heats the tissue. Charring of tissue can reduce the ability of heat to transfer through the tissue and can prevent the ablation treatment from reaching a larger area of tissue due to the reduced heat transfer. In some embodiments, the use of heat transfer fluid 140 can help to reduce or eliminate the likelihood of charring and can help to increase the area of tissue treated.

In embodiments where the heat transfer fluid 140 is injected or dispensed into tissue surrounding the catheter shaft 104, particularly the distal region 128, the heat transfer fluid 140 may be beneficial in transferring heat to a larger area of tissue. This may enable a larger area of tissue to be treated than if no fluid were injected.

Because lung tissue can be less dense than tissue in other body organs and regions (e.g., the liver), such lung tissue may have a higher resistance to heat transfer, or insulation effect, that can hamper efforts to deliver energy sufficient to treat or ablate tissue. As such, dispensing a heat transfer fluid may be more advantageous in pulmonary tissue compared to other, denser types of tissue.

In some embodiments, the heat transfer fluid 140 may comprise additional agents. For example, medicants, such as antimicrobial, antiviral, anticancer, anti-tumor, anti-inflammatory, pro-inflammatory, and other such compounds or substances may be introduced. Cells, including stem cells, as well as cell growth promoters or inhibitors may also be used. The heat transfer fluid 140 or a component thereof may also coagulate, solidify, or act as a sclerosing agent, for example after being heated, cooled, or activated (e.g., via a polymerization initiator). Such a fluid may be useful if a void is created as a result of fluid delivery or so as to encapsulate the tissue region being treated. Examples of such fluids comprise heat curing epoxies, thermoset resins (e.g., polyurethane, polyester), and protein complexes (e.g., egg whites).

The heat transfer fluid 140 may comprise visualization agents. These agents may be beneficial in indicating the extent to which the heat transfer fluid 140 has spread within the tissue being treated, and could be used to demarcate an approximate treatment area. In some embodiments, the visualization agents may comprise pigmented or colored substances. The visualization agents may also be at least partially radiopaque, or act as MRI-contrast enhancing agents. In some embodiments, the visualization agent may include antibodies or other indicators capable of binding to a particular tissue type (e.g., cellular cancer markers) so as to permit visualization of an affected region of tissue.

The catheter system 100 may also comprise additional sensors 181, 182, and/or 183. These sensors 181, 182, and/or 183 are preferably configured to monitor one or more attributes of the catheter system 100 and/or its effect on the tissue being treated. A non-limiting example of some monitored attributes that may be monitored include temperature monitoring (including for example monitoring of the wound site, of the heat transfer fluid 140, the first reagent 112, the second reagent 124, the reaction product 172, and/or of the catheter shaft 104), and monitoring of the fluid flow rate and amount thereof dispensed. Some embodiments may be configured to have one or more temperature sensors 181, 182, and/or 183 able to detect the temperature of the surrounding tissue. This temperature sensor may be attached or integrated with the catheter shaft 104, or in some embodiments may be provided as a separate temperature probe. The sensors 181, 182, and/or 183 may be able to communicate with a temperature monitoring module via printed conductive electrodes.

The catheter system 100 may be provided with a feedback mechanism 170 configured to change one or more treatment attributes based upon monitored attributes received from one or more sensors 181, 182, and/or 183 including the monitored attributes described above, or time. The feedback mechanism may be used to change treatment attributes including the amount of energy being applied to the tissue, the flow rate of the fluid, and other such attributes.

In some embodiments, the feedback mechanism may stop or decrease the application of energy via the chemical reaction and/or the heat transfer fluid 140 if the tissue or temperature increases at too high of a rate or beyond a predetermined limit. Additionally, the feedback mechanism may be used to trigger one or more predefined treatment modes, although it will be understood that such predefined treatment modes may not necessarily need to be triggered by the feedback mechanism or any monitored attribute in particular, and may be used independently of such (for example, after passage of a certain time period rather than in response to one more monitored attributes or treatment attributes). A predefined treatment mode, may, for example, include time intervals where application of energy is modulated or made intermittently active. A feedback mechanism may, for example, be used to modulate the energy applied based on the temperature, and could lower the energy applied during a predetermined time interval when the tissue reaches a certain temperature, and raise the energy applied after that time interval if the tissue temperature has decreased. It will be understood that the time intervals and other predefined treatment modes may also be determined algorithmically based on real-time monitoring of the tissue and/or the catheter system 100, and are not necessarily determined or defined prior to beginning of the treatment.

Of course, it will be clear that while the catheter shaft 104 is illustrated as a simple cylinder with a rounded distal region 128, other configurations are encompassed by the present disclosure. For example, some embodiments may utilize a catheter shaft having a flattened profile with a sharper distal region or tip. Some embodiments may be shaped for insertion into certain spaces within a patient's body. Some embodiments may be shaped to apply more energy at certain points on the surface of a catheter shaft. And some embodiments may have edges sharp enough to cut tissue, or they may be accompanied by cutting devices affixed to or used with the main device.

Although the inventions have been disclosed in the context certain embodiments and examples, those skilled in the art will understand that the present disclosure extends beyond the specifically disclosed embodiments to other alternative embodiments and/or uses of the inventions and obvious modifications and equivalents thereof. In addition, while several variations of the inventions have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes or embodiments of the disclosed inventions. Thus, it is intended that the scope of the present inventions herein disclosed should not be limited by the particular disclosed embodiments described above.

What is claimed is:

1. A device for the delivery or removal of energy to or from a region of a patient, the device comprising:
   a catheter shaft configured to be inserted into the patient to reach a treatment region;
   a first reagent positioned in the catheter shaft at about a distal region of the catheter shaft;
   a first lumen positioned within the catheter shaft configured to deliver a quantity of a limiting reagent to the distal region of the catheter shaft where the limiting reagent and the first reagent at least partially react with each other in a thermochemical reaction to produce a reaction product;
   a second lumen positioned within the catheter shaft configured to extract the reaction product from the distal region of the catheter shaft, wherein the first lumen and the second lumen are in fluid communication;
   a third lumen positioned within the catheter shaft configured to transport a heat transfer fluid to the treatment region, the heat transfer fluid configured to transfer energy between the treatment region and the reaction product, wherein the heat transfer fluid and the reaction product are distinct materials, the third lumen comprising:
      an ejection port at a distal end of the third lumen; and
      an extraction port at the distal end of the third lumen,
      wherein the ejection port is configured to allow the heat transfer fluid to flow out of the third lumen at or near the treatment region,
      wherein the extraction port is configured to extract at least some of the heat transfer fluid that flowed out of the ejection port;
   one or more sensors; and
   a handle attached at a proximal end of the catheter shaft, wherein the handle is configured to control at least one of a flow of the limiting reagent into the catheter shaft, a flow of the heat transfer fluid into the catheter shaft, and a flow rate of the reaction product,
   wherein the thermochemical reaction results in heating, cooling, or both;
   wherein the quantity of the limiting reagent provided at the distal region determines the amount of heating or cooling provided; and
   wherein the one or more sensors are configured to verify an amount of heating or cooling and provide feedback to a user.

2. The device of claim 1, wherein the limiting reagent is maintained at the distal end of the catheter shaft within the second lumen.

3. The device of claim 2, further comprising an extraction lumen configured to extract at least some of the heat transfer fluid that has been allowed to flow out of the distal region of the catheter shaft.

4. The device of claim 1, wherein the thermochemical reaction is selected from the following list: crystallization of supersaturated liquid salts, oxidation of metals, acid reactions, thermite reactions, acid/base reactions, oxidation reactions, and hydration reactions.

5. The device of claim 1, further comprising a fourth lumen configured to extract the heat transfer fluid from the catheter shaft such that the heat transfer fluid circulates within the catheter shaft without flowing out of the catheter shaft into a patient's body.

6. The device of claim 5, wherein the one or more sensors are configured to monitor inlet and outlet temperatures of the heat transfer fluid,
   wherein the one or more sensors are positioned at or near the distal tip; and
   wherein the one or more sensors communicate with a temperature monitoring module via printed conductive electrodes.

7. The device of claim 1, wherein the one or more sensors are configured to detect the temperature of the reaction product at about the distal region of the catheter shaft.

8. The device of claim 1, wherein the one or more sensors are configured to detect the temperature of the surrounding tissue.

9. The device of claim 1, further comprising a feedback mechanism configured to adjust the amount of energy transfer occurring between the reaction product and tissue of the treatment region in response to one or more monitored attributes.

10. The device of claim 9, wherein the one or more monitored attributes are selected from the group consisting of tissue temperature, reaction product temperature, flow of heat transfer fluid out of the distal region of the catheter shaft, and time.

11. The device of claim 9, wherein the feedback mechanism is configured to stop the flow of limiting reagent, stop the flow of heat transfer fluid, or both in response to a level of the one or more monitored attributes exceeding a predetermined limit.

* * * * *